(12) United States Patent
Kwak et al.

(10) Patent No.: US 6,649,697 B2
(45) Date of Patent: Nov. 18, 2003

(54) DENDRITIC POLYETHERKETONE AND HEAT-RESISTANT BLEND OF PVC WITH THE SAME

(75) Inventors: Seung-yeop Kwak, Seoul (KR); Dae-up Ahn, Seoul (KR)

(73) Assignee: Polyplus Co., Ltd. (KR)

( * ) Notice: Subject to any disclaimer, the term of this patent is extended or adjusted under 35 U.S.C. 154(b) by 19 days.

(21) Appl. No.: 10/040,461

(22) Filed: Jan. 9, 2002

(65) Prior Publication Data

US 2002/0099139 A1 Jul. 25, 2002

Related U.S. Application Data

(62) Division of application No. 09/528,511, filed on Mar. 17, 2000, now Pat. No. 6,388,011.

(30) Foreign Application Priority Data

Dec. 16, 1999 (KR) .............................. 99-58255

(51) Int. Cl.[7] .......................... C08G 65/48; C08L 27/06
(52) U.S. Cl. ...................... 525/151; 525/395; 525/471; 528/125
(58) Field of Search ................................ 525/395, 471, 525/151; 528/125

(56) References Cited

U.S. PATENT DOCUMENTS 4,045,382 A    8/1977 Braese et al. ............... 260/4 R
4,792,635 A    12/1988 Marhold et al. ............ 568/332

OTHER PUBLICATIONS

Hawker, Craig J. et al. "Hyperbranched Poly (etherketones): Mainipulation of Structure and Physical Properties" Macromolecules 29 pp 4370–4380 (1996).*

Miller, T.M. et al. "Dendritic Analogues of Enginerring Plastics: A General One–Step Synthesis of Dendritic Polyaryl Ethers," *J. Am. Chem. Soc.* (1993), vol. 115, pp. 356–357.

* cited by examiner

*Primary Examiner*—Patricia A. Short
(74) *Attorney, Agent, or Firm*—Foley & Lardner

(57) ABSTRACT

A hyperbranched polyetherketone and a heat-resistant blend of polyvinylchloride with the same. The polyethereketone is synthesized by self-polycondensation of 3,5-bis[4-[(2,3,4,5, 6-pentafluorophenyl)carbonyl]phenoxy]-4-hydroxbenzophenone or 3,5-difluoro-4-hydroxybenzophenone, and then substituting 50 to 80 mole % of fluorine atoms present in the side chains and ends of the PEK molecule by polar groups. In addition, a blend of polyvinylchloride can be manufactured using the hyperbranched polyetherketone by a melt blending technique applicable for industrial purpose at a temperature of 180 to 120° C., and thus the blend of polyvinylchloride with the polyetherekentone can be applied to high temperature end-use products such as hot water pipes.

6 Claims, 1 Drawing Sheet

DENDRITIC POLYETHERKETONE AND HEAT-RESISTANT BLEND OF PVC WITH THE SAME

BACKGROUND OF THE INVENTION

1. Field of the Invention

The present invention relates to a polyetherketone (PEK) and a heat-resistant blend of polyvinylchloride (PVC) with the same, and more particularly, to a dendritic or hyperbranched PEK which exhibits miscibility with PVC and allows for melt blending with PVC, and a heat-resistant blend of PVC with the PEK.

2. Description of the Related Art

PVC, the most common type of polymer in use, has a broad range of applications, for example, pipes, soft films for packing food, fibers, interior articles, and the like. However, PVC has a low glass transition temperature (Tg) and a low heat distortion temperature (HDT), which restricts the applications of PVC at a high-temperature range. For example, a commercial PVC exhibits a glass transition temperature of about 85° C. Thus, it would be highly desirable and commercially advantageous to improve the heat-resistance of PVC and thereby provide the PVC with higher temperature end-use applications, such as hot water pipes.

To meet this need, research into a technique for manufacturing linear polymers which exhibit a high degree of miscibility with PVC and offer high glass transition temperatures and blends of PVC with the same has been conducted. Most of linear polymers synthesized to satisfy this need further have polar groups at the backbone of common linear polymers.

For example, U.S. Pat. No. 4,698,390 teaches heat-resistant blends of PVC containing a linear polycarbonate, the glass transition temperature of which has been increased by adding sulfonic groups to the backbone of the polycarbonate. However, the problem with this PVC blend lies in the use of a solution blending method which cannot be applicable to mass production systems for commercial purpose. As another example, heat-resistant blend of PVC with polar linear polyarylates has been suggested by S. -Y. Kwak et al., in an article entitled "Effect of Molecular Structure of Polyarylates on the Compatibility in Polyarylate/PVC blends, Journal of Applied Polymer Science, 70, 2173, 1998. However, in this disclosure a solution blending method has been adopted rather than the melt blending method which is commercially practicable for the heat-resistant blends of PVC.

The difficultly in applying the melt blending method to prepare PVC blends is based on the following. First, PVC has a specific hierarchy structure and includes microcrystallites which serve to provide for physical crosslinks within the structure, so that its temperature range of melt processing is restricted, for example, to a temperature of 180 to 210° C. Second, for high temperature end-use applications of PVC, for example, for use of PVC in making hot water pipes, it is required to blend PVC with linear polymers having glass transition temperatures greater than or equal to 160° C. In addition, when the melt blending technique is applied to blend PVC with a linear polymer having such a high glass transition temperature, melt blending temperatures should be 70 to 100° C. higher than the glass transition temperature of the linear polymer added, i.e., in the range of 230 to 260° C. to allow for easy melt blending. The reason is because the linear polymer has much entanglements in the melt state. As a result, PVC which exhibits weak thermal stability deteriorates at the high temperature.

SUMMARY OF THE INVENTION

In view of the above, it is an object of the present invention to provide a hyperbranched polyetherketone (PEK) which has a glass transition temperature (Tg) above 160° C. and offers a high degree of miscibility with polyvinylchloride by melt blending at a relatively low temperature of 180 to 210° C. within a short period of time.

It is another object of the present invention to provide a heat-resistant PVC blend with the hyperbranched PEK, which is applicable to high temperature end-use products such as hot water pipes.

The first object of the present invention is achieved by a PEK synthesized by self-polycondensation of 3,5-bis[4-[(2,3,4,5,6-pentafluorophenyl)carbonyl]phenoxy]-4-hydroxybenzophenone having the formula (1)

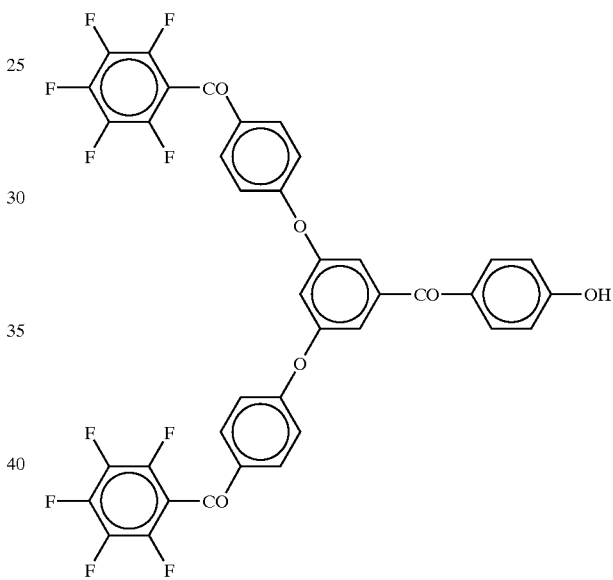

(1)

Another embodiment of the PEK according to the present invention is synthesized by fluorine substitution reaction from PEK polymerized from 3,5-difluoro4'-hydroxybenzophenone having the formula (2)

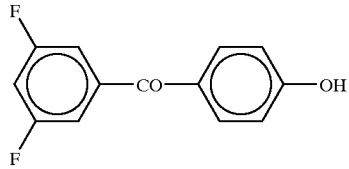

(2)

Preferably, 50 to 80 mole % of fluorine atoms present in the molecular structure of the PEK polymerized from 3,5-difluoro-4'-hydroxybenzophenone having the formula (2) hereinabove are substituted by polar groups having the formula (3)

(3)

wherein A represents

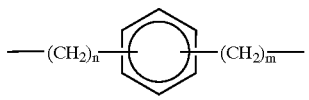

or alkylene groups of 1 to 3 carbon atoms, n has a value of from 0 to 2, and m has a value of 0 or 1, which allows for easy melt blending with PVC within a short period of time at relatively low temperatures.

Preferably, in the formula (3) A is

—$CH_2$—, —$CH_2CH_2$—, —$CH_2CH_2CH_2$—, —$CH(CH_3)$— or —$C(CH_3)_2$—.

Preferably, the degree of branching of the PEK synthesized from the monomer of formula (1) is in the range of 0.4 to 0.6.

The second object of the present invention is achieved by a blend of PVC comprising: one of the previously mentioned PEKs in a ratio of 10 to 50 percent by weight of the total blend; and PVC in a ratio of 90 to 50 percent by weight of the total blend.

Preferably, the blend of PVC is manufactured by melt blending. Also, the melt blending may be carried out at a temperature of 180 to 210° C. The blend of polyvinylchloride has a single glass transition temperature of 105° C. or more in the differential power curve obtained by differential scanning calorimetry.

The hyperbranched PEK according to the present invention has a high glass transition temperature greater than or equal to 160° C., and can be uniformly blended with PVC by melt blending at relatively low temperatures within a short period of time. Also, the hyperbranched PEK ensures that melt blending thereof with PVC is practicable for industrial use and does not cause deterioration of PVC, and thus the PVC blend with the PEK can be efficiently used in manufacturing high temperature end-use applications such as hot water pipes.

BRIEF DESCRIPTION OF THE DRAWING

The above objects and advantages of the present invention will become more apparent by describing in detail preferred embodiments thereof with reference to the attached drawing in which.

DETAILED DESCRIPTION OF THE INVENTION

Figure 1:
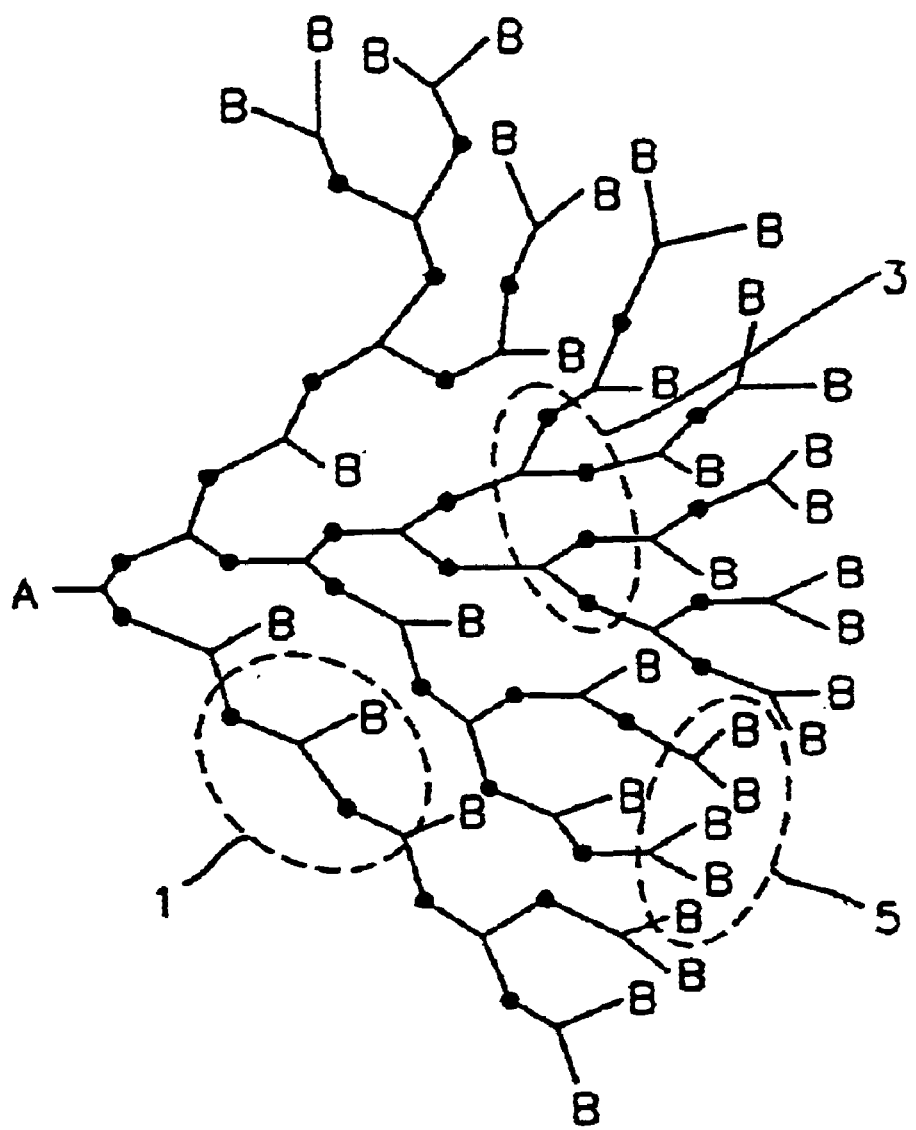
FIG. 1 illustrates the molecular structure of a hyperbranched polyetherketone (PEK) according to the present invention.

In synthesizing a preferred embodiment of polyetherketone according to the present invention, 3,5-bis[4-[(2,3,4,5,6-pentafluorophenyl)carbonyl]phenoxy]-4-hydroxybenzophenone (BPFBP) having the formula (1) hereinabove is initially self-polycondensated. In the self-polycondensation reaction, a condensation reaction between fluorine atoms and hydroxy groups occurs to form ether bonds and thus a polymer. The condensation reaction between fluorine and hydroxy groups takes place at one or two points per BPFBP repeating unit. If this condensation reaction occurs at one point per BPFBP repeating unit, a polyetherketone (PEK) having the formula (4) will be obtained.

(4)

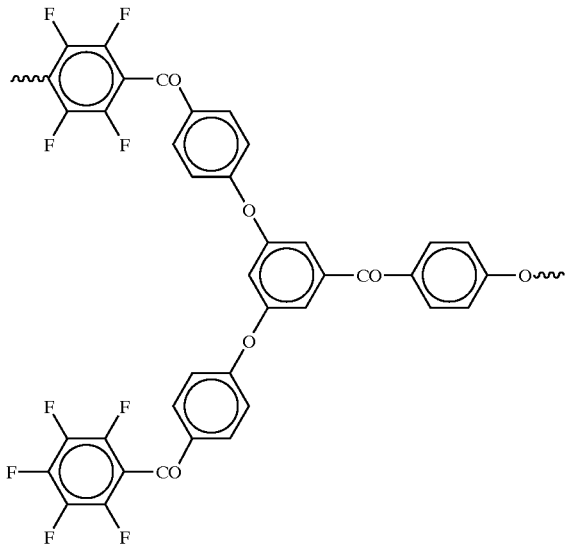

Meanwhile, if the condensation reaction between flourine and hydroxy groups occurs at two points per BPFBP repeating unit, a polyetherketon (PEK) having the formula (5) will be obtained.

(5)

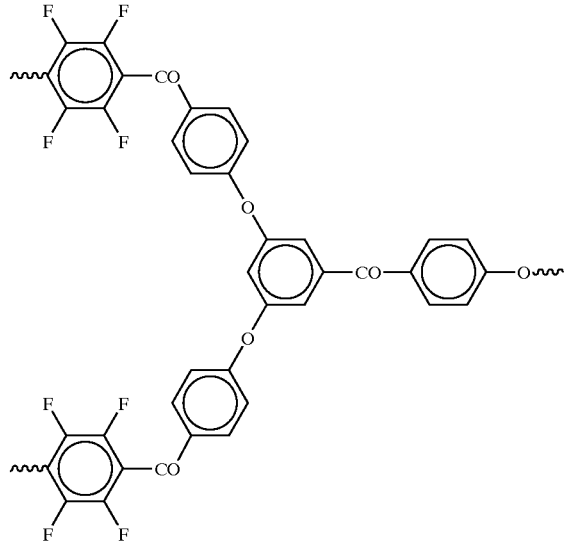

As can be noted from comparison between the formulas (4) and (5), the higher the occurrence of condensation reaction at two points per the repeating unit, the greater the number of branches in the produced PEK, resulting in hyperbranched PEKs.

Next, the hyperbranched PEK is reacted with aromatic or aliphatic cyano alcohol compounds having the formula (6) to substitute approximately 50 to 80 mole % of fluorine present in the molecular structure of the PEK by the polar groups having the formula (3) hereinabove.

(6)

wherein A represents

or alkylene groups of 1 to 3 carbon atoms, n has a value of from 0 to 2, and m has a value of 0 or 1. Preferably, A is selected from the group consisting of

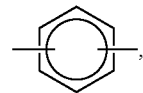

—CH$_2$—, —CH$_2$CH$_2$—, —CH$_2$CH$_2$CH$_2$—, —CH(CH$_3$)— and —C(CH$_3$)$_2$—.

The substitution reaction is carried out to ensure a high degree of miscibility and ease of melt blending with PVC, and higher glass transition temperature of the PVC blend with the PEK. The improved miscibility with PVC is due to polar-polar interaction between the polar groups substituted for fluorine and the polar PVC. Also, if it were possible for 100 mole % of fluorine in the PEK to be substituted by the polar groups described above, PEKs having the formulas (4) and (5) could be converted to PEKs having the formulas (7) and (8), respectively, by the substitution reaction.

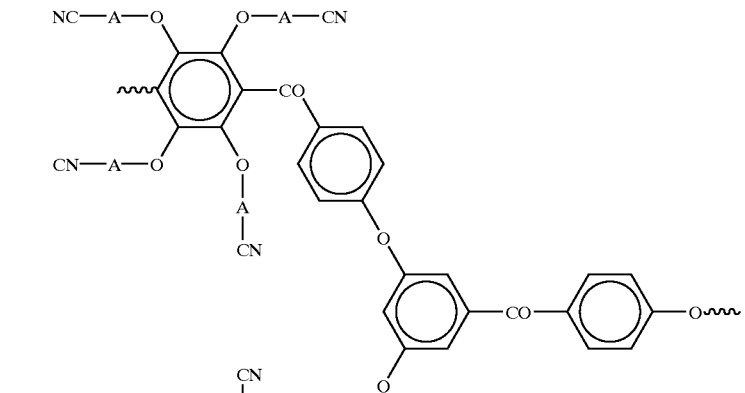
(7)

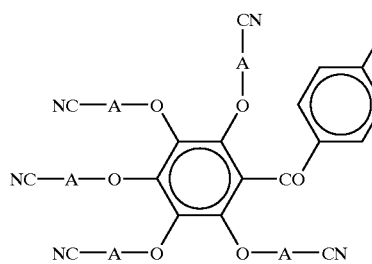

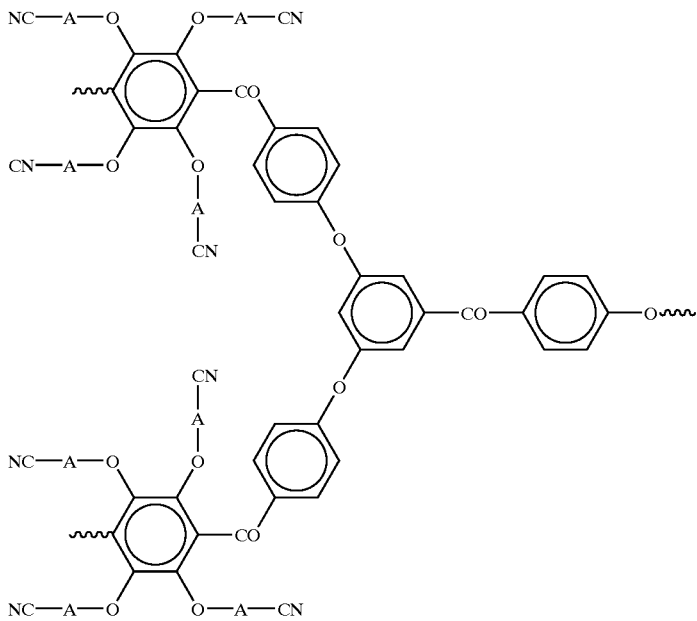
(8)

In actual reaction systems, although excess reagent given by the formula (6) is added, it is impossible to replace 100 mole % of fluorine with the polar groups. However, the degree of substitution of fluorine must be controlled by adjusting the equivalent of the reagent added so as to make the inventive PEK have sufficient miscibility and ease of melt blending with PVC. If the degree of substitution is less than 50 mole %, the polarity of PEK obtained may not be sufficient to provide a desirable miscibility and ease of melt blending with PVC. Meanwhile, since a degree of substitution above 80 mole % cannot improve the miscibility and ease of melt blending with PVC more and more, it is inefficient to increase the degree of substitution to be above 80 mole %.

Another embodiment of PEK according to the present invention is synthesized by end-group substitution reaction of the PEK polymerized from 3,5-difluoro-4'-hydroxybenzophenone (DFHBP) having the formula (2). In the self-polycondensation reaction of DFHBP, a condensation reaction between fluorine atoms and hydroxy groups occurs to form ether bonds and thus a polymer. The condensation reaction between fluorine and hydroxy groups takes place at one or two points per DFHBP repeating unit. If this condensation reaction occurs at one point per DFHBP repeating unit, a polyetherketone (PEK) having the molecular structure of the formula (9) will be obtained.

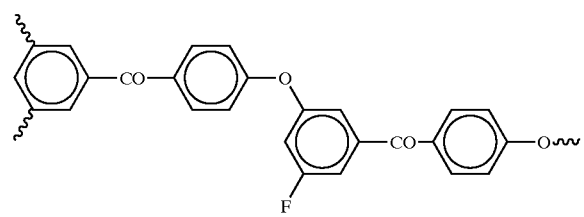

(9)

Meanwhile, if the condensation reaction between fluorine and hydroxy groups occurs at two points per DFHBP repeating unit, a polyetherketone (PEK) having the molecular structure of the formula (10) will be obtained.

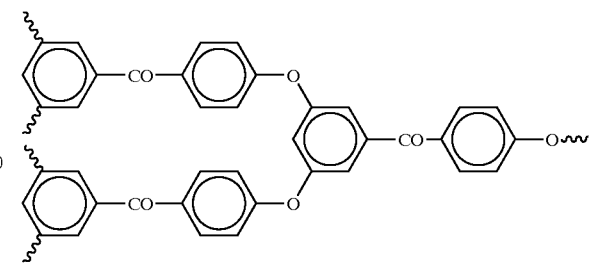

(10)

As can be noted from comparison between the formulas (9) and (10), the higher the occurrence of condensation at two points per the repeating unit, the greater the number of branches in the produced PEK, resulting in highly hyper-branched PEKs.

Next, the hyperbranched PEK is reacted with aromatic or aliphatic cyano alcohol compounds having the formula (6), which is used in the synthesis of the PEK described previously, to substitute approximately 50 to 80 mole % of fluorine present in the molecular structure of the PEK by the polar groups having the formula (3) hereinabove.

If it were possible for 100 mole % of fluorine in the PEK to be substituted by the polar groups described above, PEKs having the formulas (9) and (10) could be converted to PEKs having the formulas (11) and (12), respectively, by the substitution reaction, respectively.

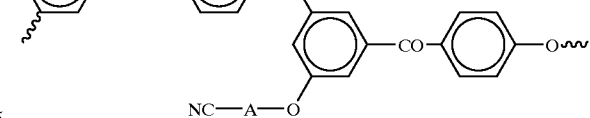

(11)

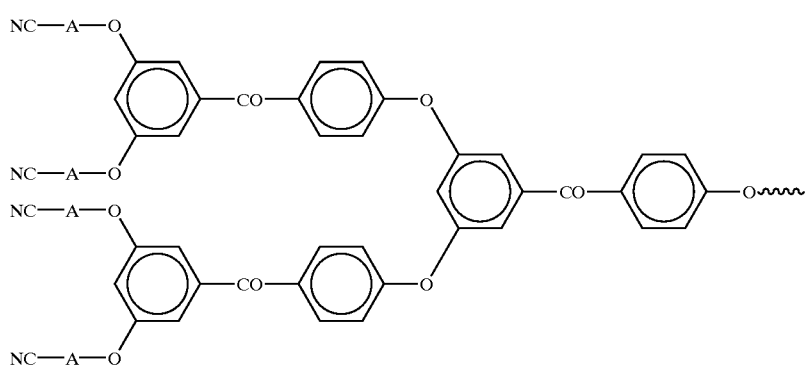

(12)

In actual reaction systems, although excess reagent given by the formula (6) is added, it is impossible to replace 100 mole % of fluorine with the polar groups. However, the degree of substitution of fluorine must be controlled by adjusting the equivalent of the reagent added so as to make the inventive PEK have sufficient miscibility and ease of melt blending with PVC.

FIG. 1 illustrates the molecular structure of a hyperbranched polyetherketone (PEK) according to the present invention. As shown in FIG. 1, the PEK, which is obtained through self-polycondensation of monomers each having $AB_2$ (herein, A represents hydroxy groups and B represents fluorine), has a hyperbranched semi-globular structure. In particular, the hyperbranched structure of PEK is comprised of linear structural units 1, branched structural units 3 and end structural units 5. Due to the many branched structural units 3 of the PEK, entanglement of molecular chains is almost non-existent, compared to linear polymers, and provides the PEK with a low melt viscosity compared to linear PEKs having similar molecular weights, which assures ease of melt blending with PVC at relatively low temperatures, that is, in the range of temperatures melt processing of PVC is practicable. In addition, it has been found that the PEK according to the present invention can be easily blended with PVC by melting in a PVC processing temperature range from 180 to 210° C. within a short period of time. Accordingly, a heat-resistant blend of PVC can be easily produced by melt blending on a commercial scale without deterioration of PVC.

Also, the PEK according to the present invention has many fluorinated end structural units 5, and thus, based on the reactivity of the fluorine, the molecular chain of the PEK can take many polar groups, which increases the glass transition temperature and the miscibility with polar PVC. To produce the higher degree of miscibility with PVC and the higher glass transition temperature of PEK, in the synthesis of the PEK according to the present invention, 50 to 80 mole % of fluorine present in the side chains and ends of the PEK molecule are substituted by aromatic or aliphatic cyano groups which induce polar-polar interaction with chlorine groups of PVC. In addition, the heat-resistant blend of PVC with the PEK exhibits a high glass transition temperature and a high heat distortion temperature (HDT), so that it is applicable to high temperature end-use products such as hot water pipes. Also, its superior miscibility with PVC assures thermal and mechanical stability after use for a longer period of time.

Preferably, the degree of branching of the PEK synthesized from the monomer of formula (1) according to the present invention is adjusted from 0.4 to 0.8. If the degree of branching is below 0.4, the amount of reactive fluorine atoms decreases, and thus the degree of substitution of polar cyano groups must be increased to above 80 mole % to assure a higher glass transition temperature and better miscibility with PVC. Also, it is unpractical to polymerize the hyperbranched is polymer to a degree of branching above 0.8.

The present invention will be described in greater detail by means of the following examples. The following examples are for illustrative purposes and not intended to limit the scope of the invention.

EXAMPLE 1

The present example provides illustration of the synthesis of 3,5-bis[4-[2,3,4,5,6-pentafluorophenyl)carbonyl] phenoxy]-4-hydroxybenzophenone (BPFBP) having the formula (1) illustrated above.

Stage 1. Synthesis of 3,5-difluoro-4-methoxybenzophenone

A 3-necked flask was charged with 30 ml of 1,2-dichloroethane, 7.6 g (70.0 mmol) of anisole, and 9.7 g (73.0 mmol) of aluminum chloride ($AlCl_3$), a catalyst for Friedel-Crafts acylation reaction. While purging the flask at room temperature with an argon gas, a solution containing 10.0 g (56.6 mmol) of 3,5-difluorobenzoylchloride dissolved in 15 ml of 1,2-dichloroethane was added dropwise to the flask and left for 14 hours for reaction. Subsequently, 20 ml of deionized water was added to the flask and stirred for 15 hours. The reaction product was poured into 200 ml of deionized water and washed three times, each time with 100 ml of methylene chloride, to extract 3,5-difluoro-4-methoxybenzophenone. The solvent was evaporated from the reaction product to give the 3,5-difluoro4-methoxybenzophenone in a yield of 97%.

Stage 2. Synthesis of 3,5-diphenoxy-4-methoxybenzophenone

This stage was for introducing phenol to the obtained 3,5-difluoro-4-methoxybenzophenone by nucleophilic aromatic substitution reaction. A 3-necked flask was charged with 6.0 g (24.2 mmol) of 3,5-difluoro-4-methoxybenzophenone, 9.0 g (95.8 mmol) of phenol, 9.0 g (65.2 mmol) of potassium carbonate ($K_2CO_3$) as a basic catalyst, 50 ml of N-methylpyrrolidone (NMP) and 20 ml of toluene, and heated to reflux toluene for 2 hours at 150° C. while pulsing the flask with an argon gas. Under the reflux, water was removed and collected in a Dean-Stark trap.

Then, the reaction temperature was raised to 200° C. for further reaction for 4 hours. After the reaction was complete, the reaction mixture was poured into 600 ml of deionized water and washed with ether to extract 3,5-diphenoxy-4-methoxybenzophenone. The ether was evaporated from the 3,5-diphenoxy-4-methoxybenzophenone and dried to give the 3,5-diphenoxy-4-methoxybenzophenone in a yield of 72%.

Stage 3. Synthesis of 3,5-bis[4-[2,3,4,5,6-pentafluorophenyl)carbonyl]phenoxy]-4-methoxybenzophenone This stage was for introducing reactive fluorine atoms to the obtained 3,5-diphenoxy-4-methoxybenzophenone to obtain 3,5-bis[4-[2,3,4,5,6-pentafluorophenyl)carbonyl] phenoxy]-4-methoxybenzophenone. A 3-necked flask was charged with 5.0 g (12.6 mmol) of the 3,5-diphenoxy-4-methoxy benzophenone, 6.5 g (48.7 mmol) of $AlCl_3$ as a catalyst for Friedel-Crafts acylation reaction, and 30 ml of 1,2-dichchloroethane. While purging the flask at room temperature with an argon gas, a solution containing 6.0 g (26.0 mmol) of pentafluorobenzoylchloride dissolved in 15 ml of 1,2-dichloroethane was added dropwise to the flask and left for 4 hours for reaction. Subsequently, 20 ml of deionized water was added to the flask and stirred for 15 hours. The reaction product was poured into 300 ml of deionized water and washed four times, each time with 100 ml of methylene chloride, to extract 3,5-bis[4-[(2,3,4,5,6-pentaflurophenyl) carbonyl]phenoxy]-4-methoxybenzophenone. The solvent was evaporated from the reaction product to give the 3,5-bis[4-[(2,3,4,5,6-pentaflurophenyl)carbonyl]phenoxy]-4-methoxybenzophenone in a yield of 83%.

Stage 4. Synthesis of BPFBP

This stage was for converting the methoxy group of the obtained 3,5-bis[4-[(2,3,4,5,6-pentaflurophenyl)carbonyl] phenoxy]-4-methoxybenzophenone to hydroxy group to synthesize the BPFBP. A 3-necked flask was charged with 5.0 g (6.4 mmol) of the 3,5-bis[4-[(2,3,4,5,6-pentaflurophenyl)carbonyl]phenoxy]-4-methoxybenzophenone, 50 ml of 48% HBr and 100 ml of glacial acetic acid, and heated to react for 15 hours under reflux. Then, the flask was cooled and excess glacial acetic acid was evaporated. The reaction product was poured into 400 ml of deionized water and washed four times, each time with 100 ml of ether. Then, the solvent was evaporated from the reaction product, which resulted in a mixture of the unreacted 3,5-bis[4-[(2,3,4,5,6-pentaflurophenyl)carbonyl]phenoxy]-4-methoxybenzophenone and the desired BPFBP. The mixture was dissolved in a 0.1N -sodium hydroxide solution and filtered to remove the precipitants. Then, a 0.1N -hydrochloric acid was added dropwise to the remaining solution, filtered and then dried to give the desired monomer BPFBP in a yield of 72%.

EXAMPLE 2

The present example provides an illustration of the synthesis of 3,5-difluoro-4'-hydroxybenzophenone (DFHBP) having the formula (2) illustrated above.

Stage 1. Synthesis of 3,5-difluoro4-methoxybenzophenone

A 3-necked flask was charged with 30 ml of 1,2-dichloroethane, 7.6 g (70.0 mmol) of anisole, and 9.7 g (73.0 mmol) of $AlCl_3$, a catalyst for Friedel-Crafts acylation reaction. While purging the flask at room temperature with an argon gas, a solution containing 10.0 g (56.6 mmol) of 3,5-difluorobenzoylchloride dissolved in 15 ml of 1,2-dichloroethane was added dropwise to the flask and left for 4 hours for reaction. Subsequently, 20 ml of deionized water was added to the flask and stirred for 15 hours. The reaction product was poured into 200 ml of deionized water and washed three times, each time with 100 ml of methylene chloride, to extract 3,5-difluoro4-methoxybenzophenone. The solvent was evaporated from the reaction product to give the 3,5-difluoro4-methoxybenzophenone in a yield of 97%.

Stage 2. Synthesis of DFHBP

This stage was for converting the methoxy group of the obtained 3,5-difluoro-4-methoxybenzophenone to hydroxy group to synthesize the DFHBP. A 3-necked flask was charged with 13.6 g (54.9 mmol) of the 3,5-difluoro-4-methoxybenzophenone, 60 ml of 48% HBr and 90 ml of glacial acetic acid, and heated to react for 15 hours under reflux. Then, the flask was cooled and excess glacial acetic acid was evaporated. The reaction product was poured into 400 ml of deionized water and washed three times, each time with 150 ml of ether. Then, the solvent was evaporated from the reaction product, which resulted in a mixture of the unreacted 3,5-difluoro-4'-methoxybenzophenone and the desired DFHBP. The mixture was dissolved in a 0.1N-sodium hydroxide solution and filtered to remove the precipitants. Then, a 0.1N-hydrochloric acid was added dropwise to the remaining solution, filtered and then dried to give the desired monomer DFHBP in a yield of 72%.

EXAMPLE 3

The present example provides an illustration of the self-polycondensation of the BPFBP having the formula (1) illustrated above.

A 3-necked flask was charged with 10 ml of NMP, 3.0 g (3.9 mmol) of BPFBP, 0.2 g (8.7 mmol) of sodium as a catalyst, and 0.1 g (0.45 mmol) of 15-crown-5. The flask was heated under reflux for 6 hours at 120° C. while purging with an argon gas, for the self-polycondensation reaction. After the reaction was complete, the reaction product was poured into 500 ml of deionized water to precipitate, and stirred at room temperature for 5 hours. Then, the precipitants were filtered, washed twice with 500 ml of methanol, and dried to give a hyperbranched PEK having reactive fluorine atoms in the side chains and ends of the molecule thereof, which has a degree of branching of 0.6, a number average molecular weight of 16,000, a polydispersity of 2.2, and a glass transition temperature of 138° C.

The degree of branching, which indicates the ratio of branched structural units present in the molecular structure, was determined by $^{19}F$ NMR spectroscopy and calculated using the following equation, as suggested by D. Hoelter et al. in an article entitled "Degree of Branching in Hyperbranched Polymers", Acta Polymer., 48, 30, 1997.

$$\text{degree of branching} = \frac{^{19}F \text{ peak area of end structural units}}{\left(\begin{array}{c} ^{19}F \text{ peak area of end structural units} + \\ ^{19}F \text{ peak area of linear structural units} \end{array}\right)}$$

Also, the molecular weight of the PEK was determined by means of gel permeation chromatography (GPC) and linear polystyrene standards were used for calculation.

EXAMPLE 4

The present example provides an illustration of the self-polycondensation of the DFHBP having the formula (2) illustrated above.

A 3-necked flask was charged with 20 ml of NMP, 15 ml of toluene, 3.0 g (14.1 mmol) of DFHBP and 2.8 g (20.0 mmol) of $K_2CO_3$ as a basic catalyst. The flask was heated to reflux toluene for 3 hours at 150° C. while purging with an argon gas. Under the reflux, water was removed and collected in a Dean-Stark trap. Then, the reaction temperature was raised to 200° C. at a rate of 5° C./min for further reaction for 3 hours. After the reaction was complete, the reaction product was poured into 800 ml of deionized water to precipitate, and stirred at room temperature for 5 hours. Then, the precipitants were filtered, washed twice with 500 ml of methanol, and dried to give a hyperbranched PEK having reactive fluorine atoms in the side chains and ends of the molecule thereof, which has a degree of branching of 0.5, a number average molecular weight of 23,000, a polydispersity of 2.5, and a glass transition temperature of 160° C.

EXAMPLE 5

This example provides an illustration of the substitution of fluorine atoms present in the side chains and ends of PEK molecule obtained in Example 3 by polar groups which improves miscibility and ease of melt blending with PVC.

A 3-necked flask was charged with 20 ml of NMP, 3.0 g of PEK obtained in Example 3, 3.0 g of one of the aromatic or aliphatic cyano alcohol compounds listed in Table 1, and 2.8 g (20.0 mmol) of $K_2CO_3$ as a basic catalyst. The flask was heated at a rate of 2° C./min while purging with an argon gas. The mixture was reacted for 3 hours and the heating temperature was varied in the range of 180 to 200° C. depending on the type of cyano alcohol compound used. After the reaction was complete, the reaction product was poured into 800 ml of deionized water to precipitate, and stirred at room temperature for 5 hours. Then, the precipitants were filtered, washed twice with 500 ml of methanol, and dried to give a hyperbranched PEK in which some of the reactive fluorine atoms present in the side chains and ends of the molecule were substituted by the aromatic or aliphatic cyano groups. The number average molecular weight, the degree of substitution by polar cyano groups, the polydispersity and the glass transition temperature for each PEK are shown in Table 1.

Table 1 shows that the substitition of some of the fluorine atoms present in the PEK molecule by aromatic cyano groups increases the glass transition temperature of the ultimate polymer product by about 33–43° C. compared to that before the substitution. For reference, the glass transisiton temperature of the PEK from Example 3 before the substitution was 138° C. This is because the effect of raising the glass transition temperature by the presence of aromatic groups and polar groups is more notable than the effect of lowering the glass transition temperature by the formation of ether bonds.

However, the substitution of some of the fluorine atoms present in the PEK molecule by aliphatic cyano groups barely changes the glass transition temperature relatiave to before the substitution. This is because the rise in glass transition temperature due to the presence of polar groups is offset by the decrease in glass transition temperature due to the presence of ether bonds and aliphatic groups.

TABLE 1

| Cyano compound reacted with PEK | Degree of substitution (%) | Number average molecular weight (g/mol) | Polydispersity | Glass transition temperature (Tg, ° C.) |
|---|---|---|---|---|
| 2-Cyanophenol | 61 | 9,000 | 1.8 | 171 |
| 3-Cyanophenol | 70 | 11,000 | 1.4 | 177 |
| 4-Cyanophenol | 66 | 10,000 | 1.7 | 181 |
| 4-Hydroxy-benzylcyanide | 78 | 15,000 | 1.6 | 175 |
| 3-Hydroxy-propionitrile | 73 | 9,000 | 1.5 | 148 |
| Lactonitrile | 68 | 7,000 | 1.7 | 133 |
| Acetone cyanohydrine | 62 | 8,000 | 1.5 | 129 |

EXAMPLE 6

The present example provides an illustration of the substitution of fluorine atoms present in the side chains and ends of the PEK molecule obtained in Example 4, which improves miscibility and ease of melt blending with PVC.

The substitution reaction of Example 5 was followed except that the PEK obtained in Example 4 was used instead of the PEK obtained in Example 3. The number average molecular weight, the degree of substitution by polar cyano groups, the polydispersity and the glass transition temperature for each PEK are shown in Table 2.

As shown in Table 2, the change in the glass transition temperature of each PEK according to the type of polar groups shows a similar pattern to that shown in Table 1.

EXAMPLE 7

The present example provides an illustration of the ease of melt blending of PVC with the PEKs obtained in Examples 5 and 6, and the superior thermal properties of PVC blends with the same.

Commercially available PVC (having a number average molecular weight of 20,000, a polydispersity of 1.5, a glass transition temperature of 83° C., obtained by suspension polymerization), and either the PEK of Example 5 or the PEK of Example 6 were mixed in a ratio of 9:1, 8:2, 7:3, 6:4 and 5:5 by weight of the total mixture (of about 40–50 g), and melt blended in an internal mixer (manufactured by Haake PolyLab Co.). As a result, all samples were uniformly blended at a temperature of 190 to 200° C. within about 450 seconds, and showed a single glass transition temperature in the differential power curve obtained by differential scanning calorimetry (DSC). Thus, it can be concluded that the PEKs of Examples 5 and 6 can be easily and uniformly mixed with PVC by melt blending.

On the other hand, it has been found that the thermal properties of PVC blends vary depending on the mixing ratio between PEK and PVC, and the type of substituted cyano groups. For the PVC blends with the PEK of Example 5, the substitution by aromatic cyano groups showed a glass transition temperature of 121 to 133° C. and a softening temperature (Vicat) of 117 to 129° C., while the substitution by aromatic cyano groups showed a glass transition temperature of 106 to 117° C. and a softening temperature of 101 to 112° C.

For the PVC blends with the PEK of Example 6, the substitution by aromatic cyano groups showed a glass transition temperature of 126 to 134° C. and a softening temperature of 120 to 130° C., while the substitution by aromatic cyano groups showed a glass transition temperature of

TABLE 2

| Cyano compound reacted with PEK | Degree of substitution (%) | Number average molecular weight (g/mol) | Polydispersity | Glass transition temperature (Tg, ° C.) |
|---|---|---|---|---|
| 2-Cyanophenol | 68 | 16,000 | 1.6 | 176 |
| 3-Cyanophenol | 77 | 21,000 | 1.5 | 183 |
| 4-Cyanophenol | 66 | 20,000 | 1.7 | 184 |
| 4-Hydroxy-benzylcyanide | 81 | 22,000 | 1.9 | 177 |
| 3-Hydroxy-propionitrile | 77 | 19,000 | 1.6 | 166 |
| Lactonitrile | 63 | 13,000 | 1.4 | 155 |
| Acetone cyanohydrine | 66 | 15,000 | 1.3 | 148 |

112 to 125° C. and a softening temperature of 106 to 121° C.

Briefly, the PVC blends with PEKs of Examples 5 and 6 according to the present invention exhibit considerably better thermal properties than pure PVC, and various heat-resistant materials can be produced by adjusting the mixing ratio of PEK and PVC and the type of polar groups introduced to PEK.

As described above, the PEKs according to the present invention ensure easy melt blending with PVC at relatively low temperatures, resulting in PVC blends having excellent heat-resistance which are applicable in manufacturing hot water pipes. The PEKs according to the present invention can extend the processing temperature range of PVC to a higher temperature limit compared to conventional PVC.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A polyetherketone synthesized by self-polycondensation of 3,5-difluoro-4'-hydroxybenzophenone having the formula (I)

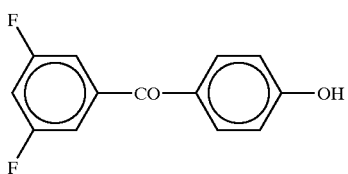
(I)

wherein 50 to 80 mole % of fluorine atoms present in the molecular structure of the polyetherkeone are substituted by polar groups having the formula (II)

—O—A—CN (II)

wherein A represents

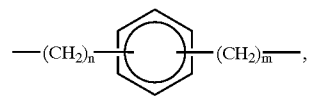

or alkylene groups of 1 to 3 carbon atoms, n has a value of from 0 to 2, and m has a value of 0 or 1.

2. The polyetherketone of claim 1, wherein A is selected from the group consisting of

—CH$_2$—, —CH$_2$CH$_2$—, —CH$_2$CH$_2$CH$_2$—, —CH(CH$_3$)— and —C(CH$_3$)$_2$—.

3. A blend of polyvinylchloride comprising:
   a polyetherketone according to claim 1 in a ratio of 10 to 50 percent by weight of the total blend; and
   polyvinylchloride in a ratio of 90 to 50 percent by weight of the total blend.

4. The blend of polyvinylchloride of claim 3, wherein the blend is manufactured by melt blending.

5. The blend of polyvinylchloride of claim 4, wherein the melt blending is carried out at a temperature of 180 to 210° C.

6. The blend of polyvinylchloride of claim 3, wherein the blend has a single glass transition temperature of 105° C. or more in a differential power curve obtained by differential scanning calorimetry.

* * * * *